US00PP10924P

United States Patent [19]

Bradford et al.

[11] Patent Number: Plant 10,924

[45] Date of Patent: May 25, 1999

[54] NECTARINE TREE NAMED 'CANDY WHITE'

[76] Inventors: Lowell Glen Bradford, 12439 E. Savana Rd.; Norman G. Bradford, 11875 E. Savana Rd., both of Le Grand, Calif. 95333

[21] Appl. No.: 08/975,097

[22] Filed: Nov. 20, 1997

[51] Int. Cl.[6] ..... A01H 5/00

[52] U.S. Cl. ..... Plt./189

[58] Field of Search ..... Plt./40.1, 41.1, Plt./41.2, 189

[56] References Cited

U.S. PATENT DOCUMENTS

P.P. 7,918 7/1992 Bradford et al. ..... Plt./41.3

P.P. 9,360 11/1995 Bradford et al. ..... Plt./40.1

*Primary Examiner*—Howard J. Locker

*Assistant Examiner*—Ashwin Mehta

[57] ABSTRACT

The present invention relates to a nectarine tree, *Prunus persica*, and more particularly to a new and distinct variety broadly characterized by a medium size, medium vigor, self-fertile, productive and regular bearing tree. The fruit matures under the ecological conditions described approximately the third week in June, with first picking on Jun. 20, 1997. The fruit is uniformly large in size, sub-acidic in flavor, globose in shape, freestone in type, very firm in texture, and nearly full red in skin color. The variety was a first generation cross using 'Ruby Diamond' (U.S. Plant Pat. No. 7,918) yellow flesh nectarine as the selected seed parent and an unnamed white flesh nectarine seedling as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally 'Candy White'. The present variety was developed by us in 1992 in a cultivated area of our experimental orchard at Bradford Farms near Le Grand, Calif. in Merced County (San Joaquin Valley). It was a first generation cross using 'Ruby Diamond' (U.S. Plant Pat. No. 7,918) nectarine as the selected seed parent and unnamed white flesh nectarine seedling as the selected pollen parent. Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The fruit produced by the present variety is most similar to the 'June Pearl' (U.S. Plant Pat. No. 9,360), by producing white flesh nectarines that are sub-acidic in flavor, firm in texture, almost full red in skin color, and virtually free from red texture bleeding, but is distinguished therefrom and an improvement thereon by producing fruit that ripens nine days later, that is sweeter in flavor, and that is freestone in type instead of clingstone.

The present variety is similar to its seed parent, 'Ruby Diamond' (U.S. Plant Pat. No. 7,918) by producing nectarines that are large sized, freestone, very firm, and nearly full red in skin color, but is very distinguished by producing fruit that is white flesh instead of yellow flesh, and that is sub-acidic in flavor instead of acidic.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard ripe on Jun. 24, 1997. All major color code designations are by reference to the Inter-Society Color Council, National Bureau of Standards. Common color names are also used occasionally.

Tree

Size: Medium, achieving a height of 8' [2.44 meters] after the fifth growing season utilizing typical dormant pruning in the plant breeding grounds.

Vigor: Medium vigor, responding satisfactorily to irrigation and fertilization.

Growth: Spreading and dense.

Form: Round topped.

Hardiness: Hardy, able to survive typical winter weather experienced in central California.

Production: Very productive, thinning necessary.

Bearing: Regular bearer, with no alternate bearing yet observed.

Fertility: Self-fertile.

Trunk:

*Size.*—Medium, reaching a diameter of 4" [102 mm.] during the fifth growing season.

*Texture.*—Medium rough, with roughness increasing with age.

*Bark Color.*—Dark grayish brown [62. d.gy.Br].

*Lenticels.*—Numerous. Color: Light grayish brown [60. l.gy.Br]. Average Size: ⅛" to ⅜" [3.2–9.5 mm.].

Branches:

*Size.*—Medium, typical of the species.

*Texture.*—Smooth on 1st year wood, increasing roughness with age.

*Color.*—1st Year wood topside: Grayish red [19. gy.R]. 1st Year wood underside: Light yellow green [119. l.YG]. Older wood: Moderate yellowish brown [77. m.yBr].

*Lenticels.*—Numerous, small. Color: Moderate orange yellow [71. m.OY]. Average size: 1/16" [1.6 mm.].

Leaves:

*Size.*—Medium. Average length: 5¾" [146.1 mm]. Average width: 1¼" [31.8 mm.].

*Thickness.*—Medium.

*Form.*—Elliptical.

*Apex.*—Acuminate.

*Base.*—Acute.

*Surface.*—Smooth.

*Color.*—Dorsal surface: Deep yellow green [118. deep YG]. Ventral surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Light yellow green [119. l.YG].

*Stipules.*—Numerous, 2 per leaf, 4–6 per growing tip. Average length: 5/16" [7.9 mm.].

*Glands.*—Numbers: 2 to 6 per leaf. Position: Alternately positioned on petiole and base of blade. Size: Large. Form: Reniform. Color: Moderate yellow green [120. m.YG].

Flower buds:

*Hardiness.*—Hardy, with respect to central California winters.

*Diameter.*—Typically ⅜" [9.5 mm.] 1 week before bloom.

*Length.*—Typically ¾" [19.1 mm] 1 week before bloom.

*Form.*—Free.

*Surface.*—Pubescent.

Flowers:

*Blooming period.*—Early as compared with other varieties.

*Onset of bloom.*—One percent on Feb. 20, 1997.

*Average diameter.*—1⅞" [47.6 mm].

*Fragrance.*—Slight to moderate.

*Type.*—Showy.

*Color.*—Pale purplish pink [252. p.pPk].

Fruit

Maturity when described. Firm eating ripe, Jun. 24, 1997.

Date of first picking: Jun. 20, 1997.

Date of last picking: Jul. 3, 1997.

Size: Uniform, large.

*Average diameter axially.*—2⅝" [66.7 mm.].

*Average transversely in suture plane.*—2⅝" [66.7 mm.].

*Typical weight.*—5.99 ounces [170 grams].

Form: Globose, uniform, slightly compressed toward the suture.

*Longitudinal section form.*—Circular.

*Transverse section through diameter.*—Circular.

Suture: An inconspicuous line extending from the base to slightly beyond the apex, having a slight depression beyond the pistil point.

Ventral surface: Rounded, lipped throughout but stronger on one side.

Lips: Unequal.

Cavity: Flaring, circular to slightly elongated in the suture plane, with suture showing on one side.

*Depth.*—⅜" [9.5 mm.].

*Breadth.*—¾" [19.1 mm.].

Base: Rounded and truncate.

Apex: Rounded.

Pistil point: Negligible in length, apical and completely depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—Some in wet conditions.

*Color.*—Very dark red [17. v.d.R] blending to moderate red [15. m.R.] over a pale yellow green [121. p.YG] background with abundant pale orange yellow [73. p.OY] freckling toward the apex.

Flesh:

*Color.*—Greenish white [153. gWhite] to the pit.

*Surface of the pit cavity.*—Covered with deep pink [3. deep Pk] to dark red [16. d.R.] fibers.

*Amygdalin.*—Scarce.

*Juice.*—Abundant, rich.

*Texture.*—Very firm, tough, crisp, non-melting.

*Fibers.*—Abundant, fine.

*Ripens.*—Evenly.

*Flavor.*—Sub-acidic, very sweet, average 18 brix.

*Aroma.*—Moderate.

*Eating quality.*—Very best.

Stone

Type: Freestone.

Form: Oval.

Base: Straight.

Apex: Acute.

Sides: Slightly unequal.

Surface: Furrowed toward the apex and pitted toward the base.

Ridges: Jagged toward the base.

Color: Moderate orange [53. m.O] through the pit wall becoming light yellowish brown [76. l.yBr] on the internal surface when first removed from fruit.

Pit wall: 5/16" [7.9 mm.] thick.

Tendency to split: Very slight.

Kernel:

*Form.*—Oval.

*Taste.*—Bitter.

*Viable.*—Yes.

*Average width.*—9/16" [14.3 mm.].

*Average length.*—¾" [19.1 mm.].

*Skin color.*—Pale yellow [89. p.Y] when first cracked.

*Pellicle color.*—Strong yellowish brown [74. s.yBr].

*Amygdalin.*—Abundant.

Use

Market: Fresh and long distance shipping.

Keeping quality: Fruit quality observed to remain in good condition in excess of 17 days in cold room at 36° Fahrenheit [2° Celsius].

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to the 'June Pearl' (U.S. Plant Pat. No. 9,360), by producing white flesh nectarines that are sub-acidic in flavor, firm in texture, almost full red in skin color, and virtually free from red texture bleeding, but is distinguished therefrom and an improvement thereon by producing fruit that ripens nine days later, that is sweeter in flavor, and that is freestone in type instead of clingstone.

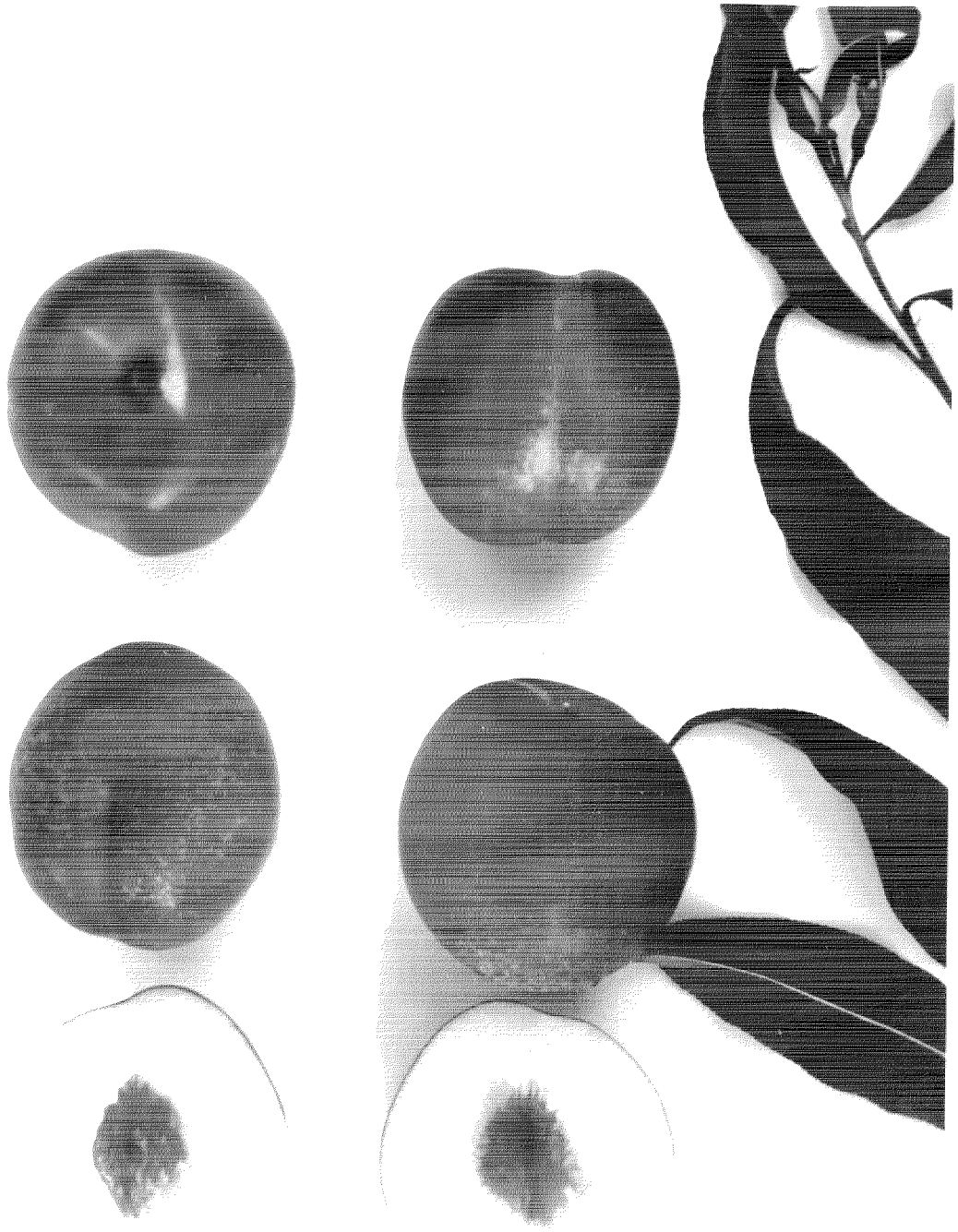

* * * * *